United States Patent
Cross, III

(10) Patent No.: US 11,154,523 B2
(45) Date of Patent: *Oct. 26, 2021

(54) COMPOSITIONS AND METHODS FOR TREATMENT OF DIABETIC NEUROPATHIES

(71) Applicant: William H. Cross, III, Waco, GA (US)

(72) Inventor: William H. Cross, III, Waco, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/264,614

(22) Filed: Jan. 31, 2019

(65) Prior Publication Data

US 2019/0231725 A1 Aug. 1, 2019

Related U.S. Application Data

(60) Provisional application No. 62/624,739, filed on Jan. 31, 2018.

(51) Int. Cl.
*A61K 31/198* (2006.01)
*A61K 31/145* (2006.01)
*A61K 31/714* (2006.01)
*A61K 31/4045* (2006.01)
*A61K 31/205* (2006.01)
*A61P 25/02* (2006.01)

(52) U.S. Cl.
CPC ......... *A61K 31/198* (2013.01); *A61K 31/145* (2013.01); *A61K 31/205* (2013.01); *A61K 31/4045* (2013.01); *A61K 31/714* (2013.01); *A61P 25/02* (2018.01)

(58) Field of Classification Search
None
See application file for complete search history.

(56) References Cited

U.S. PATENT DOCUMENTS

| | | | |
|---|---|---|---|
| 3,711,602 A | 1/1973 | Herschler | |
| 5,719,119 A | 2/1998 | Veech | |
| 7,645,742 B2 | 1/2010 | Stohs | |
| 9,414,615 B2 | 8/2016 | Sridhar | |
| 2001/0011083 A1 | 8/2001 | Barr et al. | |
| 2001/0031744 A1 | 10/2001 | Kosbab | |
| 2005/0129783 A1* | 6/2005 | McCleary | A61K 31/385 424/646 |
| 2011/0313043 A1 | 12/2011 | Kramer | |
| 2014/0044685 A1 | 2/2014 | Greenberg | |
| 2016/0228409 A1 | 8/2016 | Cross | |

FOREIGN PATENT DOCUMENTS

| | | | |
|---|---|---|---|
| IN | 1306CHE2007 | 1/2009 | |
| IN | 1306CHE2007 A * | 1/2009 | ............. A61K 48/00 |
| WO | 2008048045 | 4/2008 | |
| WO | 2013108262 | 7/2013 | |
| WO | WO-2013108262 A1 * | 7/2013 | ........... A61K 31/519 |

OTHER PUBLICATIONS

Shinohara, T., Harada, M., Ogi, K., Maruyama, M., Fujii, R., Tanaka, H., . . . & Watanabe, T. (2004). Identification ofa G protein-coupled receptor specifically responsive to β-alanine. Journal of Biological Chemistry, 279(22), 23559-23564. (Year: 2004).*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
U.S. Appl. No. 15/017,527, 20160228409, Aug. 11, 2016.
U.S. Appl. No. 15/496,919, 20180303896, Oct. 25, 2018.
U.S. Appl. No. 15/650,825, 20170312329, Sep. 6, 2019.
U.S. Appl. No. 16/264,595, 20190231806, Aug. 1, 2019.
U.S. Appl. No. 16/264,609, 20190231807, Aug. 1, 2019.
U.S. Appl. No. 16/283,660, 20190275154, Sep. 12, 2019.
Bell, D.S.H., 2012, Case Report in Endocrinology, Article ID 165056, 3pp.
Curtis, L., 2013, International Journal of Diabetes Research, 2:56-60.
Hagen, M. et al., 2017, Current Medical Research and Opinion, 33(9):1623-1634.
Henriksen, E.J., 2006, Free Radical Biology & Medicine, 40:3-12.
Lautt et al., 2010, Can. J. Physiol. Pharmacol., 88:313-323.
Shinohara, T. et al., 2004, J. Biol Chem., 279:23559-23564.
Vita Sciences, Nervex Neuropathy Pain Relief (Product Literature), Jan. 26, 2017.
Wagner, T., 2012, Pain Management, 2(3):239-250.
Wojtczak, A., 2002, Medical Teacher, 24:658-660.
Yonguc, et al., 2015, Gene, 555:119-126.

* cited by examiner

*Primary Examiner* — Dale R Miller
(74) *Attorney, Agent, or Firm* — Thomas|Horstemeyer, LLP

(57) ABSTRACT

The invention provides compositions and methods to treat diabetic neuropathies. In particular, the invention provides combinations of at least two types of antioxidants have complementary effects for use against diabetic neuropathies. The two types of antioxidants include: antioxidants that comprise stabilizing heteroatoms and antioxidants with extended conjugated segments in a ring structure. At least one of each type of provided antioxidant has a pro-oxidative or conditionally pro-oxidative effect.

15 Claims, No Drawings

COMPOSITIONS AND METHODS FOR TREATMENT OF DIABETIC NEUROPATHIES

CROSS-REFERENCE TO RELATED APPLICATIONS

This application derives priority from provisional application U.S. Ser. No. 62/624,739, filed Jan. 31, 2018 and having the same title and sole inventor.

FIELD OF THE INVENTION

The invention concerns compositions and methods for the treatment and prevention of diabetic neuropathies.

BACKGROUND

Diabetes mellitus is a carbohydrate metabolism disorder caused by insufficient insulin production and or reduced sensitivity to insulin. Consequently the cells are inhibited from normal glucose utilization, resulting in abnormally high blood sugar levels and a variety of maladies. Chronic complications include diabetic retinopathy (retinal changes leading to blindness), kidney disease and frequent infection. Acute complications from diabetes may be fatal, such as "dead-in-bed syndrome" and such as "diabetic shock" wherein a diabetic person suddenly and without warning becomes temporarily blind, disoriented and or loses consciousness during normal activity. To date there is no cure for diabetes.

Diabetes is the leading known cause for development of neuropathy in developed countries. And in fact, diabetic neuropathy affects almost 2% of the global population and about 20% of the diabetic population, and is the leading cause of morbidity and mortality in diabetes patients. It is believed to be responsible for between 50% and 75% of nontraumatic amputations. Hyperglycemia is the main risk factor, but with treatment the incidence of diabetic neuropathy is lowered almost four-fold in Type 1 diabetic patients. Other factors include the patient's age, smoking, hypertension, height and hyperlipidemia, and length of personal history with diabetes.

At an early stage diabetic neuropathies are typically associated with microvascular injuries in which blood cells supplying nerves narrow and then capillary membranes thicken, reducing the oxygen supply to nerves and resulting in ischemia of neurons. For that reason, agents that dilate blood vessels are often administered. Several other pathologies contribute. Irregularities in the polyols pathway may also contribute to microvascular damage. High glucose levels within cells also lead to non-enzymatic glycosylation of proteins, which causes inhibition of their function.

Polyneuropathies manifest in various ways. Sensorimotor polyneuropathy affects longer nerve fibers more, and reduces sensation and reflexes, appearing in the extremities first as numbness and night-time pain which may burn, ache or feel prickly.

Autonomic neuropathy affects several organ systems such as the heart, lungs, blood vessels, bones, fatty tissue, sweat glands, gastrointestinal system and genitourinary system. A common form of the disorder leads to fainting upon standing up due to orthostatic hypotension, and is also associated with respiratory sinus arrhythmia. Where the disorder affects the gastrointestinal tract it can reduce absorption of oral diabetes medications, resulting in hypoglycemia, meanwhile reduced rate of movement through the intestines can lead to bacterial overgrowth and resulting bloat, gas and diarrhea in patients with high blood sugar. Reflux nephropathy is one result for urinary symptoms, together with other outcomes when urinary retention results from urinary tract infections.

Cranial neuropathies may affect the eye's oculomotor nerve (cranial nerve #3 associated with third nerve palsy) abruptly with frontal pain, and they may begin with the nerve fibers furthest from the vascular supply. This affects eyelid movement and pupil constriction. Neuropathies that affect the sixth nerve, i.e., the abducens nerve, affect lateral eye movement. In some cases the fourth (trochlear) nerve is affected, associated with downward eye movement. Mononeuropathies of certain spinal nerves mimic the symptoms of myocardial infarction, cholecystitis or appendicitis. And entrapment neuropathies in diabetics commonly lead to carpal tunnel syndrome.

Generally neuropathic symptoms develop over a period of years. Symptoms vary between the disorders: they range from weakness, imbalance and muscle contraction; to sexual dysfunctions; to vision changes and impaired speech; to numbness or various types of pain or other sensations; to loss of control over the bladder or bowels.

Apart from control of blood sugar levels, treatment typically has the objective of managing pain and minimizing symptoms. The treatments employed fall into the following categories: tricyclic antidepressants (TCAs) at usually low dosages (for short-term relief of pain); serotonin-norepineprine reuptake inhibitors (SNRIs); selective serotonin reuptake inhibitor; antiepileptic drugs (AEDs, for short-term relief of pain); erythropoietin; natural remedies (e.g., supplements with vitamin B1, vitamin B12, alpha lipoic acid, and L-arginine to control pain); classic analgesics (opioids and or NSAIDs in combination with other treatments); medical devices (infrared, e.g., 890 nm to act upon cytochrome C to release nitric oxide and trigger vasodilation); and physical therapy (such as painless electric current to relieve stiffness, muscle training for gait and posture, exercise to minimize spasms and atrophy, ultrasound, etc.).

The mechanistic aspects of diabetic neuropathy are poorly understood so treatment has focused on symptom reduction though the disease is progressive. Even that is in need of improved approaches because, for instance, numbness in feet results in unwitting injuries, ulceration from small infections, and amputations. The problem's importance is evident in that sixty percent of lower extremity amputations are for diabetes patients. Moreover, the drugs used to treat diabetic neuropathy have a number of side effects users would not experience in their absence, thus: 38% of the users for diabetic neuropathic pain experience dizziness; 13% experience blurry vision and difficulty with depth perception; 9% experience increased neuropathy, i.e., a worsening of the pain at issue; and 14% become infected.

Consequently there is an ongoing need for compositions to treat and prevent diabetic neuropathies.

SUMMARY OF THE INVENTION

The invention provides compositions and methods to treat and prevent development of diabetic neuropathies. In particular, the present invention provides improved formulations comprising particular combinations of at least two types of antioxidants that have complementary effects for use against diabetic neuropathies. The at least two types of antioxidants include: antioxidants that comprise stabilizing heteroatoms, and antioxidants with extended conjugated segments, i.e., segments in which double bonds alternate with single bonds in a ring structure. In addition, the invention provides at least one of each type of antioxidant that further has a pro-oxidative or conditionally pro-oxidative effect. This facilitates an oxidative balance, e.g., in the liver.

In a particular embodiment the invention provides an improved composition for treatment of diabetic neuropathies, wherein said composition comprises at least two types of antioxidant compounds, characterized in that:
a) a first type of additional antioxidant compound comprises a stabilizing heteroatom covalently bonded to a saturated carbon, wherein if the heteroatom is sulfur it is not part of a disulfide bond; and
b) a second type of additional antioxidant compounds comprises an extended conjugated segment that comprises at least twelve electrons in pi bond(s) and or heteroatom electron lone pair(s) in series and participating in a ring system;
wherein:
i) the composition comprises a plurality of antioxidants in pharmaceutically effective respective amounts from each of the first and second types of antioxidant compounds; and
ii) the composition comprises at least one compound from each of the first and second types of antioxidant compounds that additionally has a pro-oxidative effect or conditionally pro-oxidative effect; and
wherein, as measured by the Neuropathic Pain Scale, the composition can decrease a user's perceived diabetic neuropathic pain by at least 50 percent within 3 to 5 days after the onset of administration.

In a further embodiment the invention provides a method for treatment of diabetic neuropathy comprising administration to a patient in need thereof a pharmaceutically effective amount of a composition comprising at least two types of antioxidant compounds, characterized in that:
a) a first type of antioxidant compound comprises a stabilizing heteroatom covalently bonded to a saturated carbon, wherein if the heteroatom is sulfur it is not part of a disulfide bond; and
b) a second type of antioxidant compound comprises an extended conjugated segment having a backbone that comprises at least twelve electrons in pi bond(s) and or heteroatom electron lone pair(s) in series and participating in a ring system;
wherein:
i) the composition comprises a plurality of antioxidants in pharmaceutically effective respective amounts from each of the first and second types of antioxidant compounds; and
ii) the composition comprises at least one compound from each of the first and second types of antioxidant compounds that additionally has a pro-oxidative effect or conditionally pro-oxidative effect; and
wherein, as measured by the Neuropathic Pain Scale, the administration decreases a user's perceived diabetic neuropathic pain by at least 50 percent within 3 to 5 days after the onset of administration.

DETAILED DESCRIPTION OF THE INVENTION

The invention may be further understood by consideration of the following definitions for the terms as used herein.

The term "diabetic" refers to the metabolic disorder diabetes mellitus and or its symptoms, and has its usual and ordinary meaning in the medicinal arts. The term includes each of the known types of diabetes including the classically defined categories of gestational diabetes, type 1 diabetes (from birth), and type 2 diabetes (later onset). The term "diabetic" further includes the five more recently classified genetically distinct groupings of patients, as follows. Cluster 1, currently known as type 1, pertains to severe autoimmune diabetes; it is characterized by insulin deficiency and the presence of autoantibodies; it has been identified in 6-15 percent of subjects. Cluster 2 pertains to severe insulin-deficient diabetes; it is characterized by younger age, insulin deficiency, and poor metabolic control, but no autoantibodies; it has been identified in 9-20 percent of subjects. Cluster 3 pertains to severe insulin-resistant diabetes; it is associated with a significantly higher risk of kidney disease and was identified in 11-17 percent of subjects. Cluster 4 pertains to mild obesity-related diabetes, most common in obese individuals, and has been identified in 18-23 percent of subjects. Cluster 5 pertains to mild age-related diabetes, especially in elderly individuals, and has been identified in 39-47 percent of subjects.

The term "diabetic neuropathy" as used herein has its usual and ordinary meaning in the medicinal arts means peripheral neuropathy due to diabetes mellitus.

The term "symptom" as used with respect to diabetic neuropathy means a symptom thereof. Numerous such symptoms are well known in the medical arts and include but are not limited to those that arise from: microvascular injuries; irregularities in the polyols pathway; and non-enzymatic glycosylation of proteins. Non-limiting examples of symptoms of neuropathies in diabetic patients include: numbness; night-time pain which may burn, ache, or feel prickly; fainting upon standing up due to orthostatic hypotension; respiratory sinus arrhythmia; hypoglycemia; bacterial overgrowth due to reduced rate of movement through the intestines and resulting in bloat, gas and diarrhea; reflux nephropathy and other outcomes when urinary tract infections cause urinary retention; frontal pain from the eye's oculomotor nerve (e.g., third nerve palsy); effects on eyelid movement and pupil constriction; sixth-nerve effects on lateral eye movement; fourth-nerve effects on downward eye movement; spinal nerve effects that mimic the symptoms of myocardial infarction, cholecystitis, and or appendicitis; and carpal tunnel syndrome due to an entrapment neuropathy; weakness; imbalance; muscle contraction; sexual dysfunction; vision changes; impaired speech; pain and other sensations; loss of control over the bladder; and loss of control over the bowels. The term "symptom" as used with respect to diabetic neuropathy is not limited by the time over which the symptom develops, regardless of whether its appearance is sudden or over a period of years.

The term "effective to reduce" as used with respect to medicinal treatment of a symptom of a diabetic neuropathy means that the compound is effective to decrease the duration or magnitude of the symptom. The term "effective to mitigate" as used with respect to medicinal treatment of a symptom of a diabetic neuropathy means that the compound is effective to decrease the discomfort or appearance that results from the symptom. The term "effective to reduce or mitigate" as used with respect to medicinal treatment of a symptom of a diabetic neuropathy does not exclude the use of any compound that both reduces and mitigates such a symptom.

The term "Neuropathic Pain Scale" or "NPS" refers to a well-validated survey-like tool in the medical arts as used to measure neuropathic pain and a drug's effectiveness in reducing and or mitigating it. For the NPS the patient scores each of ten dimensions of pain on a scale of 1 to 10, those dimensions being: intensity; sharpness; hotness; dullness;

coldness; skin sensitivity; itchiness; unpleasantness; intensity of the deep and surface pains; and duration (sporadic/intermittent, constant, or constant in the background but with flare-ups). Summing up these items gives a 100-point scale for pain. A useful benchmark of effectiveness for the present invention is that the composition lowers the perceived diabetic neuropathic pain by 50% within 3 to 5 days after the onset of administration, and virtually eliminates the pain when used daily over a period of several weeks. In certain embodiments the pain being measured is a particular pain in a particular bodily location, for instance one of: pain, burning or tingling in the feet; aching hands; painful fingers; pain in legs; back pain; retinopathy; or sciatic nerve pain.

The term "composition" as used with respect to a composition for treatment of a diabetic neuropathy means a formulation comprising one or more medicinal substances that are individually or alternatively collectively effective to minimize symptoms of a diabetic neuropathy.

The term "pharmaceutically effective amount" as used with respect to antioxidants, medicinal compounds or their salts or esters means that the respective compound(s), salt(s) or ester(s) are pharmaceutically safe and effective at the dose given. Examples of counterions and ester groups that are acceptable for pharmaceutical use are found, for instance, in editions of Remington's Pharmaceutical Sciences. Medicinal compounds for which such pharmaceutically effective amounts are particularly applicable in the present invention are folic compounds.

The terms "salts" and "esters" have their usual and ordinary meaning in organic chemistry. The term "mixtures" as used with respect to folic compounds and their salts and esters means that more than one such compound is present and that the multiple such compounds are mixed, whether they are folic compounds and or their salts and or esters.

The terms "antioxidant" and "antioxidant compound" are used interchangeably and refer to compounds that inhibit formation of free radicals by biochemical or other chemical oxidation. The term antioxidant has its usual and ordinary meaning in the chemical and medical arts.

The term "saturated carbon" as used herein refers to a carbon atom that has no multiple bonds.

The term "covalently bonded" has its usual and ordinary meaning in organic chemistry.

The term "stabilizing heteroatom" as used with respect to an atom in an antioxidant molecule means that the atom in view is an atom other than carbon, hydrogen or a metal in an organic molecule, and that the heteroatom is able to stabilize a radical formed on a neighboring saturated carbon such as by donation of electron density into it, or by rearrangement of the unpaired electron within the molecule. In particular embodiments heteroatoms N (nitrogen), S (sulfur), and or O (oxygen) are preferred in the stabilizing moiety—or moieties—in an antioxidant compound. Examples of a neighboring, i.e., adjacent, saturated hydrocarbon include —$CH_2R$, —$CHR^1R^2$, and —$CH_3$, where the R species are atoms or functional groups known in organic chemistry. Preferred examples of antioxidant compounds comprising a stabilizing heteroatom adjacent to a saturated hydrocarbon include taurine, beta-alanine, citrulline, and acetyl-L-carnitine, and in certain particularly preferred embodiments include the use of a mixture of all four.

The term "extended conjugated segment" as used with respect to an antioxidant molecule means that at least a portion of the molecule has an alternating arrangement of single and double bonds, and that the arrangement comprises at least 12 (twelve) pi electrons in pi bonds and or heteroatom lone pairs in series on a molecule. As used herein that term contemplates that the backbone of the extended conjugated segment is composed of carbon atoms, except however the backbone may include one or more heteroatoms, each being singly covalently bonded to neighboring carbon atoms or at the end of a chain of carbon atoms. The term "participating in a ring system" as used with respect to pi electrons means that their bonds are part of or define an aromatic or heteroaromatic ring. Examples of such systems with all-carbon cyclic backbones include phenyl groups and naphthalene rings. In a certain embodiment a heteroatom may be covalently double-bonded to a neighboring carbon atom and covalently single-bonded to another neighboring carbon atom, all in the extended conjugated segment. In another embodiment a heteroatom may be covalently single-bonded to each of two or three neighboring carbon atoms, but there the heteroatom has a lone pair of electrons that may participate in pi-bond delocalization as those terms are understood in organic chemistry. Examples of systems with carbon double bonds to heteroatoms in a backbone, and or with heteroatom lone pair participation in pi-bond delocalization, include pyrrole rings such as are found in hemoglobin and chlorophylls, and corrin rings such as are found in cobalamin compounds. In another embodiment a keto or enol moiety may be present in the extended conjugated segment, effectively interrupting the alternating series of single and double bonds except that keto-to-enol and enol-to-keto tautomerization allow for participation of the moiety in delocalization to either side of the moiety. Examples of systems with keto-enol participation include the curcuminoids.

The term "pro-oxidant" as used herein refers to a compound that has the ability to promote an oxidation reaction. Some antioxidant compounds act as pro-oxidants under some conditions. In a preferred embodiment the pro-oxidant activity takes place in liver tissue however the invention is not so limited. A preferred embodiment of an antioxidant compound that has a pro-oxidant effect is taurine. In certain embodiments of the invention taurine is in a mixture with at least one additional antioxidant that has a pro-oxidant effect. The term pro-oxidant as used herein includes but is not limited to compounds for which the ability to be a pro-oxidant is contingent upon conditions, such as whether dioxygen or transition metals are present. Such conditional behavior typically arises where reduction of dioxygen or peroxides is spin-forbidden and thus requires the presence of an intermediate such as a reduced transition metal—which is generated from a higher oxidation state of the metal by the action of the conditional pro-oxidant—in order to reduce the dioxygen or peroxide and have the pro-oxidant effect. The term "conditional pro-oxidant" as used herein refers to such condition-dependent pro-oxidant properties.

The term "cobalamin compound" means cobalamin—also known as Vitamin $B_{12}$—and its derivatives and variants such as salts, esters, and those defined by the bonding arrangement of functional groups at the compound's cobalt atom. Preferred cobalamin compounds have the compound's cobalt atom covalently bonded to −5'-deoxyadenosyl, —$CH_3$, —OH, or —CN; these are respectively adenosylcobalamin, methylcobalamin, hydroxocobalamin, and cyanocobalamin. Methylcobalamin is particularly preferred but the invention is not so limited.

The term "method of treatment" as used with respect to diabetic neuropathies contemplates therapeutic treatments as well as preventative treatments.

The terms "administering" and "administration" as used with respect to compounds to treat diabetic neuropathy is not limited by the type of their physical dosing, whether it is oral, buccal, parenteral, transdermal, or some other method of administering a dose.

The invention has found that diverse types of antioxidants have combined effects that reduce or mitigate the symptoms of diabetic neuropathies. In particular it is beneficial to use a combination of an antioxidant that comprises a stabilizing heteroatom and an antioxidant that has an extended conjugated segment, and to employ more than one from each type in the combination. It has further been discovered that for purposes of the invention it is beneficial if at least one of the antioxidants from each of the two categories facilitates an oxidative balance, i.e., has a pro-oxidant effect. A non-limiting example of sites for the pro-oxidant effect is the liver.

Particularly suitable compositions for the invention include a combination of two or more of the ingredients indicated in Table I in the amounts shown. These are antioxidants bearing heteroatom-stabilized saturated carbon atoms.

are: 40 to 360 mg; 80 to 320 mg; 120 to 280 mg; 160 to 240 mg; or about 200 mg. As to beta-alanine the ranges are: 10 to 90 mg; 20 to 80 mg; 30 to 70 mg; 40 to 60 mg; or about 50 mg. As to acetyl-L-carnitine the ranges are: 40 to 360 mg; 80 to 320 mg; 120 to 280 mg; 160 to 240 mg; or about 200 mg. As to theanine the ranges are: 15 to 155 mg; 35 to 135 mg; 55 to 115 mg; 75 to 95 mg; or about 85 mg.

In certain preferred embodiments the composition provides an amount of citrulline in the ranges of: 20 to 180 mg; 40 to 160 mg; 60 to 140 mg; 80 to 120 mg; or about 100 mg.

Particularly suitable compositions for the invention further include a combination of two or more of the ingredients indicated in Table II in the amounts shown. These are antioxidants bearing extended conjugation in a segment that participates in a ring structure. Technically some may also have heteroatoms neighboring saturated carbon atoms, however for purposes of the invention the conjugation is regarded as determinative of their classification. The tracing

TABLE I

| COMPOUND DESCRIPTION AND USE | STRUCTURE |
|---|---|
| Taurine in a range of 40 to 360 mg; a non-limiting illustrative quantity is 200 mg. Taurine is an antioxidant that comprises a stabilizing heteroatom, relieves oxidative stress, and has a pro-oxidative effect in the liver. | 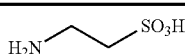<br>Taurine |
| Beta-alanine in a range of 10 to 90 mg; a non-limiting illustrative quantity is 50 mg. Beta-alanine is an antioxidant that comprises a stabilizing heteroatom. Yet beta-alanine allows the balance between antioxidants and pro-oxidants to remain stable in tissues. | 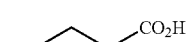<br>Beta-alanine |
| Acetyl-L-carnitine in a range of 40 to 360 mg; a non-limiting illustrative quantity is 200 mg. Acetyl-L-carnitine is an antioxidant that comprises a stabilizing heteroatom, relieves oxidative stress, and has a pro-oxidative effect in the liver. | 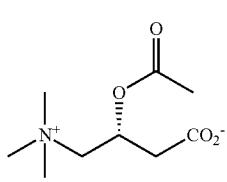<br>Acetyl-L-carnitine |
| Theanine in a range of 15 to 155 mg; a non-limiting illustrative quantity is 85 mg. Theanine is an antioxidant that comprises a stabilizing heteroatom and relieves oxidative stress. | 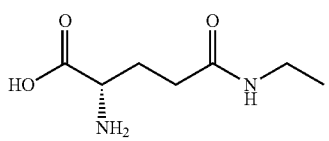<br>Theanine |
| L-Citrulline in a range of 20 to 180 mg; a non-limiting illustrative quantity is 100 mg. Citrulline, an alpha-amino acid, is an antioxidant that comprises a stabilizing heteroatom, relieves oxidative stress in endothelial tissue, and is an essential substrate in enhancing NO-depending signaling. | 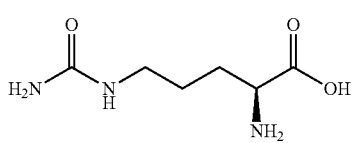<br>Citrulline |

The use of one or more additional antioxidants that comprise a stabilizing heteroatom adjacent to a saturated carbon atom may include taurine, beta-alanine, citrulline and acetyl-L-carnitine, and is particularly preferred in combination but the invention is not so limited. In certain preferred embodiments the composition provides the antioxidants shown here in the following ranges. As to taurine the ranges of pi electrons in series can be understood with melatonin as and example: its 12 pi electrons may be observed by tracing the series in a particular resonance structure in the following order: —O(:)—C=C—C=C—N(:)—C=C—C=C—, where the pi-electron lone pairs are shown in parentheses for each of the heteroatoms and where each double bond has two pi-electrons.

TABLE II

| COMPOUND DESCRIPTION AND USE | STRUCTURE |
|---|---|
| Methylcobalamin (a form of Vitamin $B_{12}$) in a range of 40 to 440 µg; a non-limiting illustrative quantity is 240 µg. Methylcobalamin is an antioxidant that comprises a conjugated segment; the segment contains nitrogen atoms and among other properties can bind the oxidant nitric oxide (NO). | 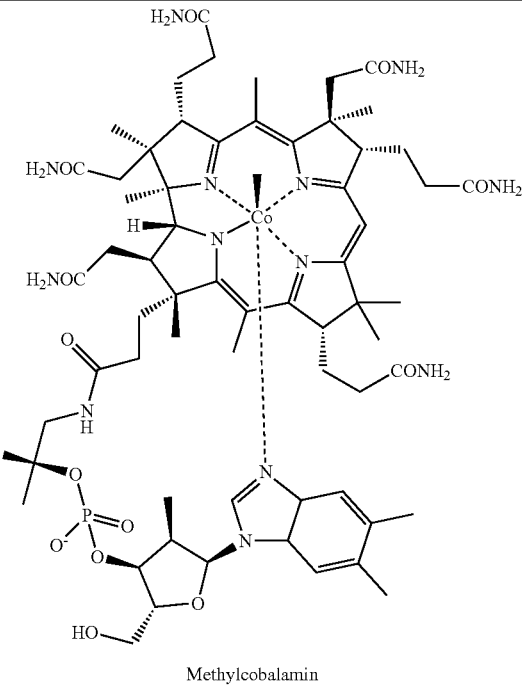<br>Methylcobalamin |
| Melatonin in a range of 1 to 50 mg; a non-limiting illustrative quantity is 30 mg. Melatonin is a weak antioxidant containing a stabilizing heteroatom and conjugated segment. It is a highly efficient direct free-radical scavenger; also stimulates antioxidant enzymes; reduces the activation of pro-oxidant enzymes; yet maintains homeostasis in the mitochondria, where 90% of the body's oxidation activity occurs. In addition melatonin is a conditional pro-oxidant. | <br>Melatonin |

Additional compounds include porphyrin ring compounds, corrin ring compounds and the like. In particular it has been useful to include cobalamin compounds in compositions of the invention. In certain preferred embodiments the composition provides a cobalamin compound in the ranges of: 40 to 440 µg; 90 to 390 µg; 140 to 340 µg; 190 to 290 µg; or about 240 µg. In some preferred embodiments the cobalamin compound is methylcobalamin. For purposes of the present invention it is useful to provide the porphyrin or corrin ring compound in the same ranges that would be provided for the cobalamin compound, e.g., 40 to 440 µg. As to melatonin some useful ranges are: 1 to 50 mg; 5 to 45 mg; 10 to 40 mg; 20 to 35 mg; or about 30 mg.

In certain embodiments the composition comprises an antioxidant bearing a phenolic or phenolic-like group. Non-limiting illustrative embodiments include at least one phenolic compound such as gallic acid, gallocatechin, catechingallate, epigallocatechin, epicatechingallate, and or epigallocatechingallate. In certain non-limiting illustrative embodiments the composition provides one or more of these compounds in a range: 5 to 500 mg; 50 to 400 mg; 100 to 300 mg; 150 to 250 mg; or about 200 mg.

By way of example a phenolic-like group is an aromatic or heteroaromatic ring that has a pendant group containing a heteroatom; examples of such pendant groups include —$ZH_{a\geq1}$ and —$ZHR_{a\geq0}$, where Z is a heteroatom such as N, S, or where the ring is heteroaromatic, O.

In some embodiments the composition comprises an antioxidant in which a hydrogen atom may be readily abstracted from a heteroatom that is not pendant upon an aromatic or heteroaromatic ring. Nonlimiting illustrative embodiments of such antioxidants include those with sulfhydryl (—SH) groups, such as cysteine and glutathione.

In certain embodiments compositions of the invention comprise one or more adjuvants. Non-limiting illustrative examples of such adjuvants include: analgesic adjuvants; inorganic compounds such as aluminum and or phosphate compounds; a mineral oil such as paraffin oil; dead bacteria such as *Bordetella pertussis, Mycobacterium bovis*, and toxoids; organic compounds such as squalene; delivery systems such as detergents; plant saponins; cytokines; combinations such as Freund's complete or Freund's incomplete adjuvant; and food-based oils such as Adjuvant 65, which is based on peanut oil. The terms in this paragraph are used with their usual and ordinary meaning in the art of formulation for drugs and dietary supplements.

In various embodiments compositions of the invention comprise one or more excipients. Non-limiting illustrative examples of such excipients include: antiadherents, binders, coatings, colors; disintegrants; flavors; glidants; lubricants; preservatives; sorbents; sweeteners; and vehicles. The terms in this paragraph are used with their usual and ordinary meaning in the art of drug formulation.

There are several survey-like tools to measure neuropathic pain and a drug's effectiveness in reducing and or mitigating it. The Neuropathic Pain Scale is particularly well-validated. For the NPS the patient scores each of ten dimensions of pain on a scale of 1 to 10, those dimensions being: intensity; sharpness; hotness; dullness; coldness; skin sensitivity; itchiness; unpleasantness; intensity of the deep and surface pains; and duration (sporadic/intermittent, constant, or constant in the background but with flare-ups). Summing up these items gives a 100-point scale for pain. A useful benchmark of effectiveness for the present invention is that the composition lowers the perceived diabetic neuropathic pain by 50% within 3 to 5 days after the onset of administration, and virtually eliminates the pain when used daily over a period of several weeks. In certain embodiments the pain being measured is a particular pain in a particular bodily location, for instance one of: pain, burning or tingling in the feet; aching hands; painful fingers; pain in legs; back pain; retinopathy; or sciatic nerve pain.

Consideration of Table III and the Examples may further clarify the scope of the invention.

µg methylcobalamin, and 15 mg melatonin. The patient was a college-age type 1 diabetic male with a persistent history of diabetic neuropathic pain. For the first five days the patient took 6 capsules daily one hour before his nightly sleep. After the first five days the patient took 2 capsules daily one hour before his nightly sleep. Pain was noted to decrease by at least 50% within 48 hours, and to be virtually eliminated over a period of one week of following this regime. Ceasing to use the formula resulted in the slow return of neuropathic pain over a period of 72 hours, and this was noticeable even by the end of the first day of non-use. The formula was particularly useful for taking before sleep as it allowed for a good night's rest, which was not obtained with use of commercially available anti-diabetes drugs alone.

In general, virtual elimination of the diabetic neuropathic pain symptoms is to be expected over a break-in period of

TABLE III

| EXAMPLE | HETEROATOM-STABILIZED ANTIOXIDANTS | EXTENDED-CONJUGATION ANTIOXIDANTS | ANTIOXIDANTS FROM OTHER CATEGORIES |
|---|---|---|---|
| 1 | 200 mg taurine<br>50 mg beta-alanine<br>200 mg acetyl-L-carnitine<br>85 mg theanine | 240 µg methylcobalamin<br>30 mg melatonin | |
| 2 | 40 mg taurine<br>10 mg beta-alanine<br>40 mg acetyl-L-carnitine<br>15 mg theanine | 40 µg methylcobalamin<br>1 mg melatonin | |
| 3 | 360 mg taurine<br>90 mg beta-alanine<br>360 mg acetyl-L-carnitine<br>155 mg theanine | 45 µg methylcobalamin<br>50 mg melatonin | |
| 4 | 300 mg taurine<br>20 mg beta-alanine<br>60 mg acetyl-L-carnitine<br>130 mg theanine | 150 µg methylcobalamin<br>40 mg melatonine | |
| 5 | 85 mg taurine<br>30 mg beta-alanine<br>250 mg acetyl-L-carnitine<br>50 mg theanine | 400 µg methylcobalamin<br>20 mg melatonine | |
| 6 | 200 mg taurine<br>50 mg beta-alanine<br>200 mg acetyl-L-carnitine<br>85 mg theanine<br>100 mg citrulline | 240 µg methylcobalamin<br>15 mg melatonin | |
| 7 | 200 mg taurine<br>200 mg acetyl-L-carnitine | 240 µg 5-adenosylcobalamin<br>30 mg melatonin | 200 mg epigallocatechin-gallate |
| 8 | 100 mg taurine<br>100 mg acetyl-L-carnitine<br>50 mg glutathione | 80 µg hydroxocobalamin<br>30 mg melatonin | |
| 9 | 100 mg acetyl-L-carnitine<br>50 mg glutathione | 80 µg cyanocobalamin<br>30 mg melatonin | 100 mg epigallocatechin |
| 10 | 100 mg acetyl-L-carnitine<br>50 mg citrulline<br>50 mg cysteine | 300 µg chlorophyll A<br>40 mg melatonin | 120 µg Alpha-lipoic acid |

Example 11

A solid dose in the form of a gel capsule was prepared containing 200 mg taurine, 50 mg beta-alanine, 100 mg citrulline, 200 mg acetyl-L-carnitine, 85 mg theanine, 240 one week to one month, with little or no pain thereafter as long as the nightly dosing with the composition continues to be maintained.

The embodiments of the invention as described herein are merely illustrative and are not exclusive. Numerous additions, variations, derivations, permutations, equivalents, combinations and modifications of the above-described invention will be apparent to persons of ordinary skill in the relevant arts and are within the scope and spirit of the invention. The invention as described herein contemplates the use of those alternative embodiments without limitation.

The invention claimed is:

1. A therapeutic method for treatment of diabetic neuropathy comprising therapeutic administration to a patient in need thereof a pharmaceutically effective amount of a composition comprising at least two types of antioxidant compounds comprising:
   a) a pharmaceutically effective amount of at least one of a first type of antioxidant compound selected from the group consisting of taurine, beta-alanine, acetyl-L-carnitine, theanine, and L-citrulline; and
   b) a pharmaceutically effective amount of at least one of a second type of antioxidant compound selected from the group consisting of a cobalamin compound and melatonin;
   wherein, as measured by the Neuropathic Pain Scale, when administration provides no antioxidants other than those named above, the administration decreases a user's perceived diabetic neuropathic pain by at least 50 percent within 3 to 5 days after the onset of administration.

2. The method of claim 1, wherein the composition comprises at least four of the first type of antioxidant compound, and the at least four compounds include taurine, beta-alanine, acetyl-L-carnitine and theanine.

3. The method of claim 1, wherein the composition comprises at least two of the second type of antioxidant compound, and the at least two compounds include melatonin and a cobalamin compound.

4. The method of claim 1, wherein the cobalamin compound is methylcobalamin.

5. The method of claim 1, wherein taurine is in the amount from 40 mg to 360 mg.

6. The method of claim 1, wherein acetyl-L-carnitine is in the amount from 40 mg to 360 mg.

7. The method of claim 1, wherein melatonin is in the amount from 1 mg to 50 mg.

8. The method of claim 1 wherein the composition comprises:
   a) taurine in an amount selected from the range of 40 mg to 360 mg;
   b) beta-alanine in an amount selected from the range of 10 mg to 90 mg;
   c) acetyl-L-carnitine in an amount selected from the range of 40 mg to 360 mg;
   d) theanine in an amount selected from the range of 15 mg to 155 mg;
   e) melatonin in an amount selected from the range of 1 mg to 50 mg; and
   f) methylcobalamin in an amount selected from the range of 40 μg to 440 μg.

9. The method of claim 1 wherein the composition comprises:
   a) taurine in an amount of 200 mg;
   b) beta-alanine in an amount of 50 mg;
   c) acetyl-L-carnitine in an amount of 200 mg;
   d) theanine in an amount of 85 mg;
   e) melatonin in an amount of 30 mg; and
   f) methylcobalamin in an amount of 240 μg.

10. The method of claim 1, wherein the cobalamin compound is selected from the group consisting of adenosylcobalamin, methylcobalamin, hydroxycobalamin, or cyanocobalamin.

11. The method of claim 1, wherein the cobalamin compound is in the amount of from 40 μg to 440 μg in the composition.

12. The method of claim 1, wherein the composition further comprises an adjuvant.

13. The method of claim 1, wherein the composition further comprises an excipient.

14. The method of claim 1, wherein the composition is in a solid dose form.

15. The method of claim 1, wherein the pain comprises burning or tingling in the feet; aching hands; painful fingers; pain in legs; back pain; retinopathy; or sciatic nerve pain.

* * * * *